United States Patent [19]

Wadsworth

[11] 4,079,469

[45] Mar. 21, 1978

[54] ELBOW JOINT ENDOPROSTHESIS

[76] Inventor: Thomas Gordon Wadsworth, 22 Hyde Park Square, London, England, W.2

[21] Appl. No.: 749,037

[22] Filed: Dec. 9, 1976

[51] Int. Cl.² .............................................. A61F 1/24
[52] U.S. Cl. ..................................... 3/1.91; 128/92 C
[58] Field of Search .................................. 3/1.9–1.913, 3/1; 128/92 C

[56] References Cited

U.S. PATENT DOCUMENTS

| | | | |
|---|---|---|---|
| 3,547,115 | 12/1970 | Stevens | 3/1.91 X |
| 3,798,679 | 3/1974 | Ewald | 3/1.91 |
| 3,816,854 | 6/1974 | Schlein | 3/1.91 |
| 3,852,831 | 12/1974 | Dee | 3/1.91 |
| 3,869,729 | 3/1975 | Attenborough | 3/1.91 |
| 3,919,725 | 11/1975 | Swanson et al. | 3/1.91 |
| 3,990,116 | 11/1976 | Fixel et al. | 3/1.91 |

*Primary Examiner*—Ronald L. Frinks
*Attorney, Agent, or Firm*—Carroll F. Palmer

[57] ABSTRACT

A bone joint endoprosthesis is formed of a proximal member and a distal member. The former is a semi-cylindrical profiled body having a proximal flat chordal surface and a semi-circular T-slot concentric with the joint axis opening distally. The latter comprises an intramedullary stem and a proximal arcuate segment of I-shape cross-section whose free end is slidably carried in the T-slot. The unit allows for normal flexion and extension motion and joint stability is provided by the T-slot arrangement of the joint articulation.

10 Claims, 9 Drawing Figures

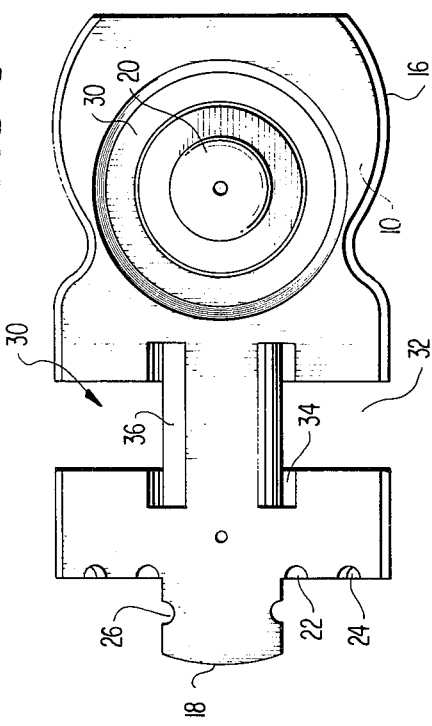
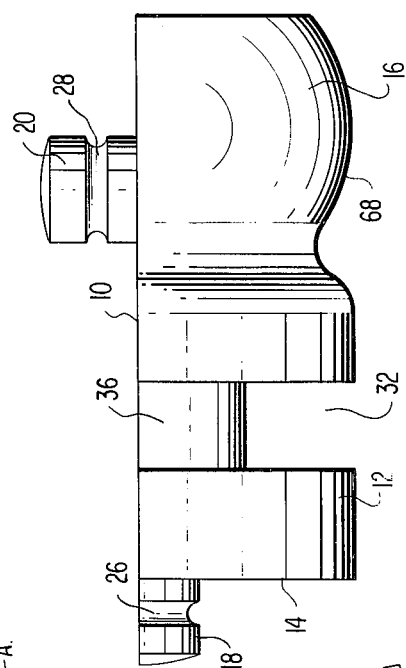
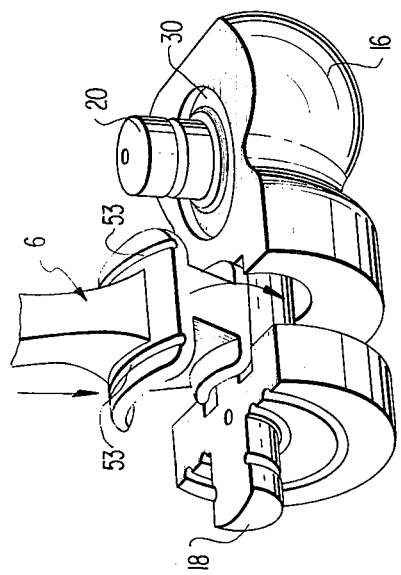
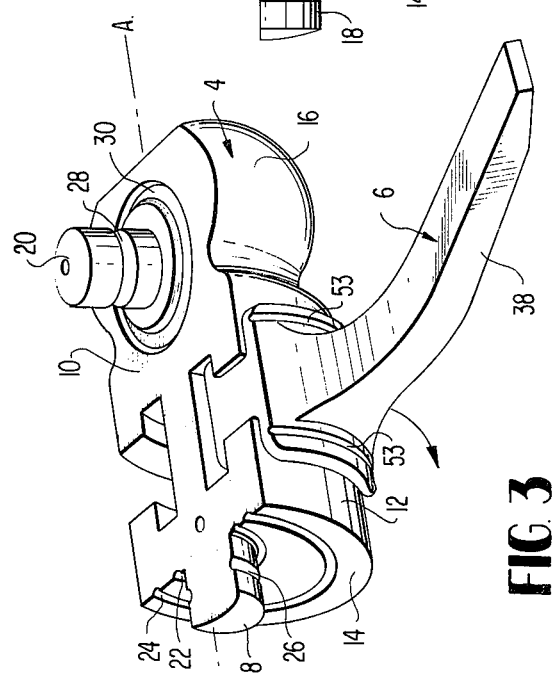
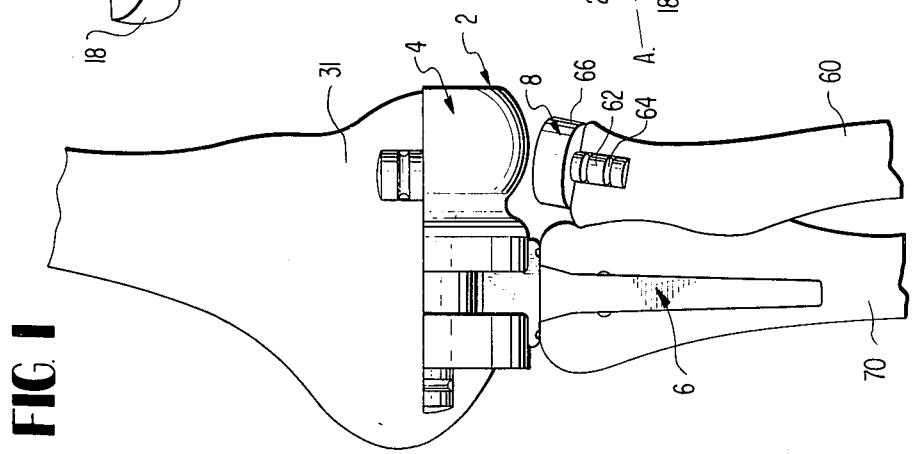

ELBOW JOINT ENDOPROSTHESIS

BACKGROUND OF THE INVENTION

1. Field of the Invention

This invention relates to bone joint prosthesis. More specifically, it concerns an elbow endoprosthesis providing good joint stability with allowance for normal flexion and extension motion at the elbow.

2. Description of the Prior Art

Use of bone joint prosthesis may be indicated for use for various derangements of the joint in which reasonable function has been lost and where there is significant stiffening and/or pain. Such conditions include osteoartheosis, which is usually secondary to trauma in the case of the elbow, rheumatoid disease and neuropathic arthropathy where there is, typically, instability.

Joint stability is a critical factor in the mobilization of weight-bearing joints as in the reconstruction of the hip and knee. It is also important in the non-weight-bearing elbow joint. On the other hand, in the elbow, unlike many other joints, no position of ankylosis is favorable to function; there may be a particular problem with regard to loss of upper limb function in the rheumatoid patient because of concomitant disease elsewhere in the limb. In short, the elbow presents special problems in prosthetic reconstruction. Hence, the following description is directed primary to elbow prosthesis, but the procedures and devices as described can find application in other bone joint reconstructions.

A variety of procedures and devices have been devised for elbow prosthetic reconstruction. Excision arthroplasty has been historically used and may involve partial or total resection of the elbow joint. Certain indications, for this operation are tuberculosis, recent comminuted fracture, old un-reduced fracture-dislocation, rheumatoid arthritis and osteoarthritis following injury. Although many patients have obtained worthwhile results, this has not been a universally successful procedure.

Early attempts at replacement arthroplasty involved the use of various materials to surface the reconstructed elbow joint: muscle and fascial flap, periosteal flaps, yellow wax and lanolin, magnesium and other metal sheets, deep fascia from the thigh and skin from the buttock. None of these have yet received popular acceptance and most are now probably of historical interest only.

In recent times there has been increasing interest in replacement arthroplasty of the elbow joint.

Partial, or hemi, replacement of the joint has been described: acrylic replacement of the distal humerus, vitallium replacement of the distal humerus, vitallium replacement of the olecranon and silastic replacement of the radial head.

Attempts have now been made to functionally replace the elbow as a whole by a 'total elbow prosthesis'. The majority of these consist of a hinge device with three parts (humeral component, ulnar component and an axis pin): all require a significant removal of bone, soft tissue dissection and reaming of the humeral and ulnar shafts in order to seat the stems of the prosthesis, which are cemented in place. Examples of this type of prosthesis include metal stems with plastic and metal axis or metal stems and metal axis. There is a more recent prosthesis which consists of two metal stems with a high density polyethylene 'clip-on' device for locking the two together, but with this there is a great deal of side-to-side instability. Another total elbow prosthesis consists of simple surfacing of the humerus with metal and the ulna with high density polyethylene. Also there is a one-piece silastic hinge with the stems inserting into the humerus and ulna; but here medial and lateral instability has to be controlled by constructing new collateral ligaments from fascia.

In so far as structural bone joint prosttheses are concerned, numerous patents have issued covering such devices of which the following is a representative listing: U.S. Pat. Nos. 2,784,416; 3,748,662; 3,798,679; 3,801,990; 3,840,905; 3,869,729 and 3,886,599.

The normal elbow is a simple and stable hinge joint permitting only flexion and extension; forearm rotation occurs at the radio-ulnar joints and the superior radio-ulnar joint is enclosed with the elbow joint in a common capsule. Severe restriction of movement or in stability of the elbow is difficult to treat. Excision arthroplasty has the distinct potential for significant instability, likewise the various joint lining procedures. Hemi-arthroplasties, as for the humerus or olecranon, do not deal with what is usually total joint surface involvement. The many hinge joints with an axis demand considerable removal of bone for insertion: many of these fail, with loosening of one or both stems of the prosthesis, and necessary removal of such a prosthesis results in serious instability of the elbow.

In spite of the numerous procedures and devices previously developed and used for elbow reconstruction, there exists a need for further improvement particularly as regards resulting joint stability, minimal removal of bone for insertion and allowance for normal flexion and extension motion.

OBJECTS

A principal object of the present invention is the provision of new forms of bone joint prostheses.

Another object is the provision of elbow endoprosthesis that present as advantages:

(i) Minimal removal of bone for insertion.

(ii) Protection of the ulnar nerve within the cubital tunnel by preservation of the medial lip of the trochlea.

(iii) Allowance for normal flexion and extension motion at the elbow.

(iv) Stability, which is importantly achieved by the arrangement of the joint articulation that guards against undue medial and lateral movement which would be abnormal for the elbow.

(v) Additional over-all stability that ensues from minimal interference with ligaments and capsule associated with the operative technique.

(vi) The prosthesis is light in weight.

(vii) Relatively cheap to produce.

(viii) Should removal of the implant be necessary, e.g. for infection, the patient would be left with a conventional excision arthroplasty which should give useful function.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by the formation of a bone joint endoprosthesis with a proximal member comprising a semi-cylindrical profiled body having a longitudinal axis concentric with the joint axis of the endoprosthesis, the proximal member having a proximal flat chordal surface, a principal body portion, a semi-globular portion coaxial with said principal body portion providing a distal surface to act as a bearing surface and a semi-circular T-slot in the principal body portion concentric with said longitudinal axis.

There is also a distal member which comprises an intramedullary stem and a proximal arculate segment of I-shape cross-section integral with the stem, the unattached end of the segment being of size to fit within the T-slot of the proximal member and hold the distal member in sliding engagement with said proximal member.

In the preferred form, the proximal member is a humeral member with a flat radial lateral surface and two keys by which to fix the member to the humeral bone. Also, the distal member is an ulnar member and the endoprosthesis may further include a button implant to replace the elbow radial head to bear upon the semi-globular portion of the humeral member.

BRIEF DESCRIPTION OF THE DRAWINGS

A more complete understanding of the new bone joint endoprosthesis of the invention may be had by reference to the accompanying drawings in which:

FIG. 1 is an anterior elevation of an elbow endoprosthesis of the invention illustrated as implanted in the humerus, ulna and radius.

FIG. 2 is a perspective view illustrating the assembling of members of the elbow endoprosthesis.

FIG. 3 is a perspective view supplementing FIG. 2.

FIG. 4 is a proximal end view of the humeral member of the elbow endoprosthesis.

FIG. 5 is an anterior elevation of the humeral member.

DESCRIPTION OF THE PREFERRED EMBODIMENTS

Figure 6:
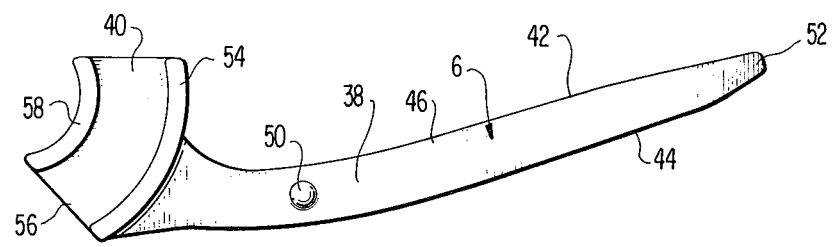
FIG. 6 is a lateral elevation of the ulnar member of the elbow endoprosthesis.
Figure 7:
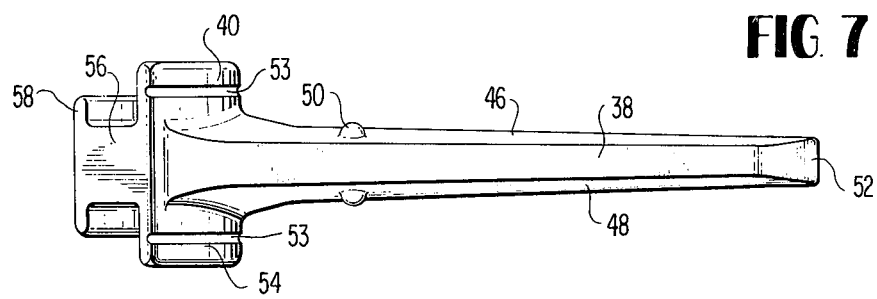
FIG. 7 is a plan view of the ulnar member.

Referring in detail to the drawings, the elbow endoprosthesis 2 basically comprises a humeral member 4 and an ulnar member 6. Optionally, it may comprise a radial member 8.

The humeral member 4 is a substantially semi-cylindrical profiled body having a longitudinal axis A—A coincident with the joint axis of the elbow prosthesis. It has a proximal flat chordal surface 10, a principal body portion 12, a flat radial lateral surface 14, a semi-globular portion 16 presenting a flat lateral surface 17, a semi-cylindrical key 18 extending medially of said lateral surface 14 and a cylindrical key 20 extending proximal of the chordal surface 10.

The lateral surface 14 carries a pair of semi-circular grooves 22 and 24. Similar grooves 26 and 28 are provided in keys 18 and 20 respectively. A circular moat 30 surrounds the key 20. These elements 22-30 assist the implantion of the member 4 in the humerus 31.

The humeral member principal body portion 12 has a semi-circular T-slot 30 formed by a radial slot portion 32 and an annular portion 34 surrounding the column 36.

The ulnar member 6 comprises an intramedullary stem 38 and a proximal segment 40 integral with the stem 38. The stem may be of trapezoidal or rectangular section with faces 42 and 44 and lateral sides 46 and 48. The sides carry a pair of small nipples 50. Preferably the end 52 of the stem 38 is tapered and grooves 53 are provided to assist in cementing member 6 to the ulna.

Figure 8:
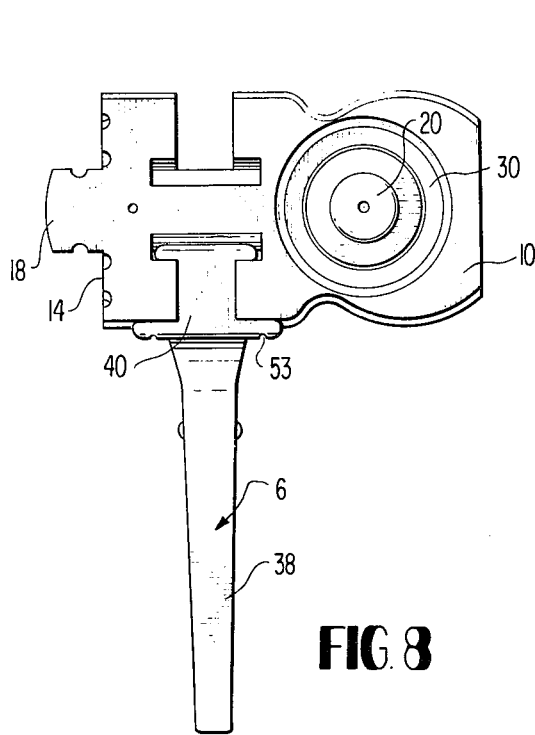
FIG. 8 is a proximal end view of the combination of humeral member and ulnar member.
Figure 9:
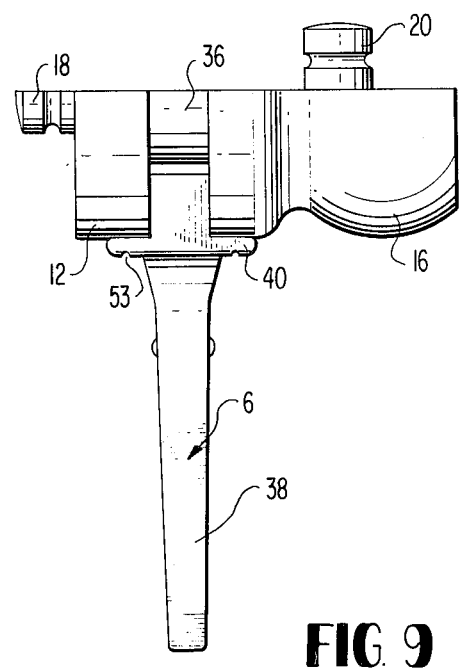
FIG. 9 is an anterior elevation of that combination.

The segment 40 is an annulus concentric with the axis A—A of I-shape cross-section comprising a base part 54, radial web 56 and proximal part 58. The width of the radial web 56 is slightly less than the width of slot portion 32 and the distant between inside surfaces of parts 54 and 58 is only slightly larger than the depth of slot portion 32 so that the segment 40 fits snugly in the T-slot 30 (see FIG. 8). In order to avoid undue strain on the joint, one may provide a little lateral and medial looseness at the prosthetic articulation.

A preferred form of the new endoprosthesis 2 includes the button implant 8 to replace a portion of the head of the radius 60. This comprises distal key portion 62 with peripheral grooves 64 and an attached proximal bearing element 66. The element 66 in movement of the implanted prosthesis 2 will ride upon the articular surface 68 of the semi-globular portion 16, as well as the normal radial notch of the ulna.

In some circumstances the implant 8 may be omitted so that the unaltered head of the radius 60 will bear on the surface 68.

The parts of the endoprosthesis as described above may be fabricated from various materials known to be acceptable for construction of endoprostheses. Advantageously, the humeral member 4 is formed of high-density polyethylene and the members 6 and 8 are made of chrome cobalt.

The axis of motion of the new elbow endoprosthesis is similar to that of the normal elbow. Also, its use requires only minimal removal of bone, less than for the usual excision arthroplasty procedure. It may be used for the right or left elbow.

The prosthesis is readily inserted, using a posterior approach to the elbow joint. After removal of part of the articulating end of the lower humerus, preserving the medial lip of the trochlea, and reaming the humeral bone to receive the two keys 18 and 20, the articular surface of the olecranon is trimmed and the medullary cavity of the ulna 70 is reamed to receive the stem 38 of the ulnar member 6. Following a successful trial fit, the ulnar member 6 is cemented in place, e.g. with methyl methacrylate. After setting of the ulnar member 6, the humeral member 4 is slotted on the ulnar component (see FIG. 2) and then cemented onto the humerus 31 with suitable forward angulation. Closure of the wound follows.

An important feature of the new elbow endoprosthesis is the simple, but effective, stability factor of the articulation of the two components. This is the T-slot of the high density polyethylene humeral member 4 and the metal segment 40 of the ulnar member 6 which slots into it. The design of the endoprosthesis ensures stability whilst permitting normal flexion and extension movement at the elbow. Important protection is afforded the ulnar nerve, within the cubital tunnel, by preservation of the medial lip of the trochlea. The superior key 20 and medial key 18 of the humeral member 4 slot into the prepared cavities and cement in the lower humerus for secure fixation and the prosthesis is also cemented to the medial lip of the trochlea. The normal lower humeral angle is simulated by proper alignment of the humeral component.

If necessary, the radial head may be removed and replaced by the metal implant 8 which is secured with cement.

The elbow prosthesis provides for total replacement of the elbow joint, without excess removal of bone, and allows for movement in the direction of the normal elbow, but with an important stability factor.

The embodiments of the invention in which an exclusive property of privilege is claimed are defined as follows:

1. An elbow endoprosthesis comprising:
   a humeral member and an ulnar member,
   said humeral member being a substantially semi-cylindrical, profiled body having a longitudinal axis coincident with the joint axis of the elbow endoprosthesis and comprising:
      a proximal flat chordal surface,
      a principal body portion,
      a flat radial lateral surface upon one side of said principal body portion,
      a semi-globular portion upon the other side of said principal body portion,
      a semi-cylindrical key extending medially of said lateral surface, and
      a cylindrical key extending proximal of said chordal surface,
   said ulnar member comprising:
      an intramedullary stem and
      a proximal segment integral with said stem,
      said segment comprising:
         a first annulus concentric with said joint axis and
         a T-shaped portion extending proximally of said annulus, the base of T being longitudinally aligned with said stem with the top of the T being a second annulus concentric with said first annulus,
   said humeral member principal body portion having a semi-circular T-slot concentric with said joint axis sized to slidably receive the T-shaped portion of said ulnar member.

2. The endoprosthesis of claim 1 which includes a button implant to replace a portion of the elbow radial head.

3. The endoprosthesis of claim 2 wherein said button implant comprises a proximal bearing element and a distal key portion.

4. The endoprostheses of claim 1 wherein said intramedullary stem includes a pair of opposed nipples distal of said segment.

5. The endoprosthesis of claim 1 wherein said keys of said humeral member have at least one peripheral groove therein.

6. The endoprosthesis of claim 1 wherein said humeral member is formed of plastic.

7. The endoprosthesis of claim 6 wherein said plastic is high density polyethylene.

8. The endoprosthesis of claim 1 wherein said ulnar member is made of metal.

9. The endoprosthesis of claim 8 wherein said metal is chrome cobalt.

10. A bone joint endoprosthesis comprising:
    a proximal member and a distal member
    said proximal member being a substantially semi-cylindrical profiled body having a longitudinal axis concentric with the joint axis of the endoprosthesis and comprising
       a proximal flat chordal surface,
       a principal body portion
       a semi-globular portion coaxial with said principal body portion providing a distal surface to act as a bearing surface and
       a semi-circular T-slot in said principal body portion concentric with said longitudinal axis,
    said distal member comprising
       an intramedullary stem and
       a proximal arcuate segment of I-shape cross-section integral with said stem, the proximal part of said segment being of size to fit within said T-slot and hold said distal member in sliding engagement with said proximal member.

* * * * *

UNITED STATES PATENT OFFICE
CERTIFICATE OF CORRECTION

PATENT NO. : 4,079,469

DATED : March 21, 1978

INVENTOR(S) : Thomas G. Wadsworth

It is certified that error appears in the above-identified patent and that said Letters Patent are hereby corrected as shown below:

Facesheet, Column 1, between side headings [22] and [51] insert:

--[30] Foreign Application Priority Data
December 12, 1975   United Kingdom ... 51118/75 --

Signed and Sealed this

Fifth Day of June 1979

[SEAL]

Attest:

RUTH C. MASON
Attesting Officer

DONALD W. BANNER
Commissioner of Patents and Trademarks